United States Patent
Qu et al.

(10) Patent No.: US 10,966,650 B2
(45) Date of Patent: Apr. 6, 2021

(54) METHOD AND DEVICE FOR DETECTING ATRIAL FIBRILLATION IN THE PRESENCE OF VENTRICULAR PACING

(71) Applicant: PACESETTER, INC., Sylmar, CA (US)

(72) Inventors: Fujian Qu, San Jose, CA (US); Stuart Rosenberg, Castaic, CA (US); Xing Pei, Thousand Oaks, CA (US); Carin Folman, Bedford, MA (US); Jennifer Rhude, Carbondale, IL (US)

(73) Assignee: PACESETTER, INC., Sylmar, CA (US)

( * ) Notice: Subject to any disclaimer, the term of this patent is extended or adjusted under 35 U.S.C. 154(b) by 344 days.

(21) Appl. No.: 16/128,234

(22) Filed: Sep. 11, 2018

(65) Prior Publication Data

US 2020/0077910 A1    Mar. 12, 2020

(51) Int. Cl.
| | | |
|---|---|---|
| *A61B 5/36* | (2021.01) | |
| *A61B 5/361* | (2021.01) | |
| *A61N 1/02* | (2006.01) | |
| *A61N 1/37* | (2006.01) | |

(52) U.S. Cl.
CPC .............. *A61B 5/361* (2021.01); *A61N 1/025* (2013.01); *A61N 1/3704* (2013.01)

(58) Field of Classification Search
CPC ....... A61B 5/046; A61N 1/025; A61N 1/3704
See application file for complete search history.

(56) References Cited

U.S. PATENT DOCUMENTS

| | | | |
|---|---|---|---|
| 8,121,675 B2 | 2/2012 | Shaquer et al. | |
| 2019/0336032 A1* | 11/2019 | Gill | A61B 5/0031 |

* cited by examiner

*Primary Examiner* — Catherine M Voorhees
*Assistant Examiner* — Roland Dinga
(74) *Attorney, Agent, or Firm* — The Small Patent Law Group LLC; Dean D. Small

(57) ABSTRACT

Methods and systems are provided for detecting arrhythmias in cardiac activity is provided. The method and systems are under control of one or more processors configured with specific executable instructions. The method and systems obtain a far field cardiac activity (CA) signal that includes a series of beats, the CA signal including paced events. The method and systems identify the paced events in the CA signals. The method and systems determine a score based on an amount of paced events and adjust at least one parameter of an atrial fibrillation (AF) detection process based on the score.

22 Claims, 5 Drawing Sheets

METHOD AND DEVICE FOR DETECTING ATRIAL FIBRILLATION IN THE PRESENCE OF VENTRICULAR PACING

FIELD OF THE INVENTION

Embodiments herein generally relate to implantable medical devices, and more particularly to detecting atrial fibrillation (AF) in the presence of ventricular pacing by the implantable medical device.

BACKGROUND OF THE INVENTION

Atrial Fibrillation (AF) is the most common cardiac arrhythmia and is strongly associated with stroke risk and a variety of cardiovascular conditions. Early AF detection is important, but can be challenging due to the often silent and intermittent nature of the rhythm disturbance.

A single-chamber implantable medical device (IMD) only detects suspected AF if the ventricular response exceeds the programmed ventricular arrhythmia detection rate, and the VTNF discrimination criteria indicate that the ventricular rate is irregular. Some patients with IMDs may exhibit an elevated risk of stroke. Accordingly, opportunity remains to reduce or avoid under-detection of AF, particularly when ventricular rates fall below a ventricular arrhythmia detection cutoff rate. Integrating floating atrial electrodes into a ventricular lead may overcome this limitation, but at the expense of added lead complexity and uncertain atrial sensing. A single chamber IMD may detect AF without an atrial lead based on the characteristics of R-R interval variability.

In addition, implantable cardiac monitors (ICMs) are provided that utilize alternative AF detection algorithms. The AF detection algorithms of at least some conventional ICMs are based on the detection of R waves and R-R interval variability. However, AF detection algorithms that are utilized in ICMs cannot readily be utilized in a single chamber IMD that delivers pacing therapy. Single-chamber IMDs deliver ventricular pacing pulses that interfere with the intrinsic atrioventricular conduction of the heart and reduce the degree of R-R interval variability, which may lead to under-detection of AF by conventional AF detection algorithms used in ICMs.

SUMMARY

A computer implemented method for detecting arrhythmias in cardiac activity is provided. The method is under control of one or more processors configured with specific executable instructions. The method includes obtaining a far field cardiac activity (CA) signals that includes a series of beats, the CA signals including paced events. The method includes identifying the paced events in the CA signals, and determining a score based on an amount of paced events. The method includes adjusting at least one parameter of an atrial fibrillation (AF) detection process based on the score.

Optionally, the method includes analyzing the CA signals to identify a i) first count of a total number of events in the CA signals, ii) second count of a number of V-paced events in the CA signals and iii) third count of a number of consecutive V-paced events in the CA signals, the score based on at least one of the first, second and third counts. Additionally or alternatively, the method includes determining an overall pacing incidence score based on a weighted combination of a total pacing incidence score and a consecutive pacing incidence score, the total pacing incidence score based on a relation between the number of the paced events and the total number of events, the consecutive pacing incidence score based on the number of consecutive V-paced events and the total number of events. Optionally, the method includes comparing the score to an upper limit and based on the comparing, stopping an AF onset process and registering the CA signals as unclassified.

Additionally or alternatively, the adjusting further comprises at least one of i) adjusting an AF onset criteria, ii) adjusting an AF exit criteria, iii) adjusting a sudden onset (SO) criteria or iv) modify an SO calculation. Optionally, the method includes when the score is between the upper and lower limits, performing at least one of the adjusting operations. Additionally or alternatively, the method includes adjusting an AF onset criteria by reducing at least one of an AF probability threshold or a number of consecutive beats to satisfy the AF probability threshold. Optionally, the method includes adjusting further comprises adjusting an AF exit criteria by reducing at least one of an AF probability threshold or a number of consecutive beats to satisfy the AF probability threshold.

Optionally, the method includes adjusting further comprises modifying the SO calculation by calculating a number of beats in the CA signals that exhibit a sudden onset value that exceeds a predetermined SO limit, and, when the number of beats exceeds an SO count limit, declaring sudden onset to be present in the CA signals. Additionally or alternatively, the method includes determining operation further comprises identifying non-conducted ventricular events in the CA signals, counting a total number of events in the CA signals, adjusting the counter by removing the non-conducted ventricular events from the count and determining the score based on the paced events and the count of the total number of events in the CA signals adjusted for the non-conducted ventricular events.

A system for discriminating rhythm patterns in cardiac activity is provided. The system includes at least one processor and a memory coupled to the at least one processor, wherein the memory stores program instructions. The program instructions are executable by the at least one processor. The system obtains a far field cardiac activity (CA) signal that includes far field CA signals for a series of beats, the CA signals including paced events. The system identifies the paced events in the CA signals, and determine a score based on the paced events. The system adjusts at least one parameter of an atrial fibrillation (AF) detection process based on the score.

Optionally, the processor is further configured to analyze the CA signals to identify a i) first count of a total number of events in the CA signals, ii) second count of a number of V-paced events in the CA signals and iii) third count of a number of consecutive V-paced events in the CA signals, the score based on at least one of the first, second and third counts. Additionally or alternatively, the processor is further configured to determine an overall pacing incidence score based on a weighted combination of a total pacing incidence score and a consecutive pacing incidence score, the total pacing incidence score based on a relation between the number of the paced events and the total number of events, the consecutive pacing incidence score based on the number of consecutive V-paced events and the total number of events.

Additionally or alternatively, the processor is further configured to compare the score to an upper limit and based on the comparison, stop an AF onset process and registering the CA signals as unclassified. Optionally, the processor is further configured to at least one of i) adjust an AF onset criteria, ii) adjust an AF exit criteria, iii) adjust a sudden onset (SO) criteria or iv) modify an SO calculation. Additionally or alternatively, the processor is further configured to, when the score is between the upper and lower limits, perform at least one of the adjusting operations.

Optionally, the processor is further configured to adjust an AF onset criteria by reducing at least one of an AF probability threshold or a number of consecutive beats to satisfy the AF probability threshold. Additionally or alternatively, the processor is further configured to adjust an AF exit criteria by reducing at least one of an AF probability threshold or a number of consecutive beats to satisfy the AF probability threshold. Optionally, the processor is further configured to modify the SO calculation by calculating a number of beats in the CA signals that exhibit a sudden onset value that exceeds a predetermined SO limit, and, when the number of beats exceeds an SO count limit, declare sudden onset to be present in the CA signals. Optionally, the processor is further configured to identify non-conducted ventricular events in the CA signals, counting a total number of events in the CA signals, adjust the counter by removing the non-conducted ventricular events from the count and determine the score based on the paced events and the count of the total number of events in the CA signals adjusted for the non-conducted ventricular events.

DETAILED DESCRIPTION

In accordance with embodiments herein, methods and devices are described for detecting and discriminating atrial fibrillation (AF), even in the presence of ventricular paced events. Methods and devices herein track incidents of ventricular pacing and, based thereon, calculate pacing incidents scores. From the pacing incidents scores, embodiments herein determine whether AF episodes can be reliably detected/declared, from cardiac activity (CA) signals analyzed by an AF detection algorithm. In addition, from the pacing incidents scores, embodiments herein may adjust one or more parameters of the AF detection algorithm in order to better account for a presence of paced events within the CA signals being analyzed.

Figure 1:
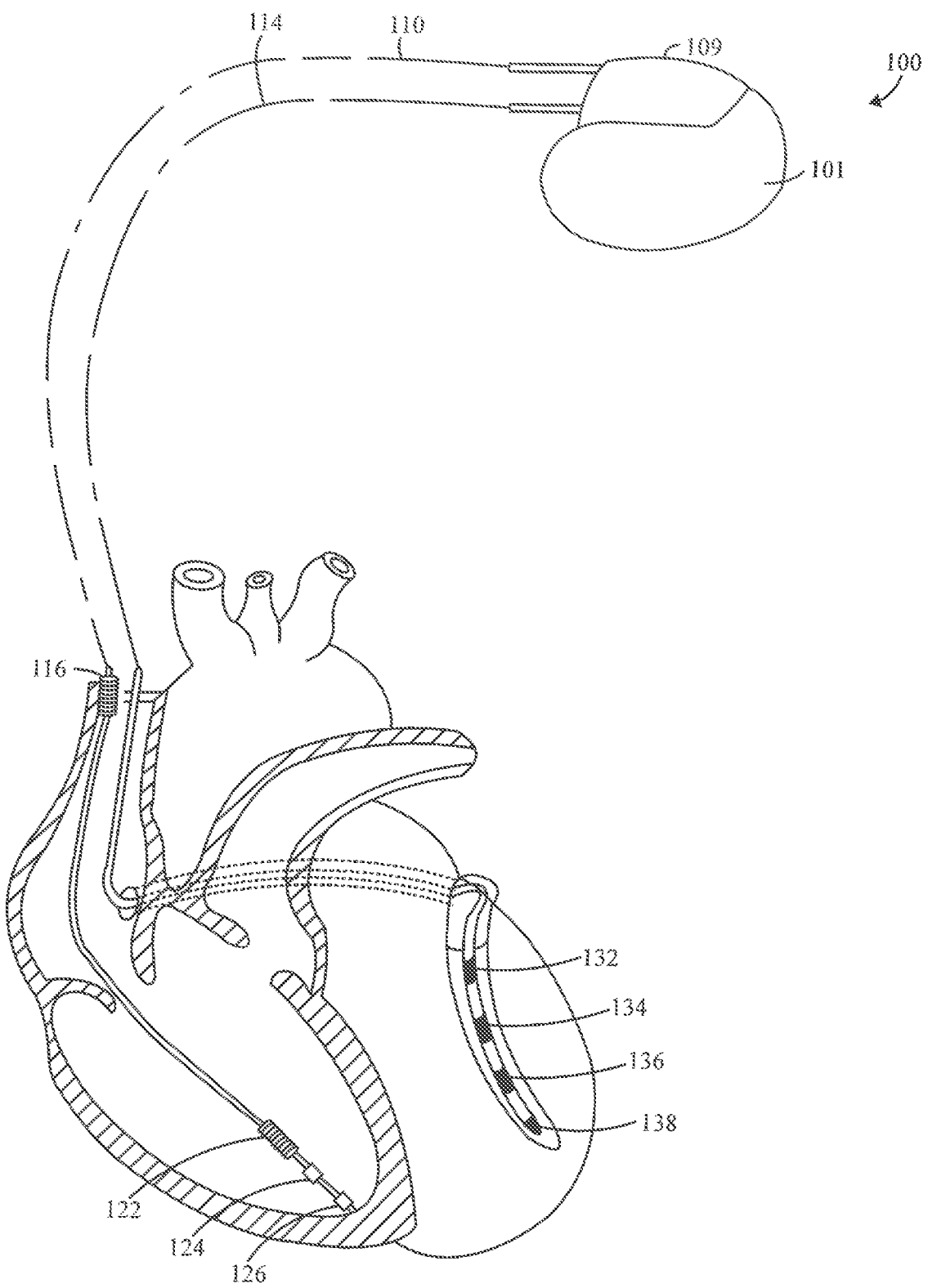
FIG. 1 illustrates an implantable medical devices (IMD) device intended for subcutaneous implantation at a site near the heart in accordance with embodiments herein.

FIG. 1 illustrates an implantable medical device (IMD) device intended for subcutaneous implantation at a site near the heart 111, in accordance with embodiments herein. The IMD 100 may be a single-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like. The IMD 100 may include a housing 101 to hold the electronic/computing components. The housing 101 (which is often referred to as the "can", "case", "encasing", or "case electrode") may be programmably selected to act as the return electrode for certain stimulus modes. The housing 101 further includes a connector 109 with a plurality of terminals 200-210 (shown in FIG. 2).

The housing 101 is joined to a header assembly 109 that holds receptacle connectors connected to a right ventricular (RV) lead 110 and optionally may also be connected to a left ventricular (LV) lead 114. The leads 110 and 114 measure cardiac signals in the ventricles of the heart. The coronary sinus lead 114 includes multiple LV electrodes 132-138 (e.g., also referred to as P1, M1, M2 and D1) to form a multi-pole LV electrode combination. The RV dual-coil lead 110 includes an RV tip electrode 126, an RV ring electrode 124, an RV coil electrode 122, and an SVC coil electrode 116. Alternatively, other types of RV coil leads such as single-coil RV lead without the coil electrode 116, can be used. The leads 110 and 114 detect intracardiac electrogram (IEGM) signals that are processed and analyzed and deliver therapies, as described herein.

Implantable Medical Device

Figure 2:
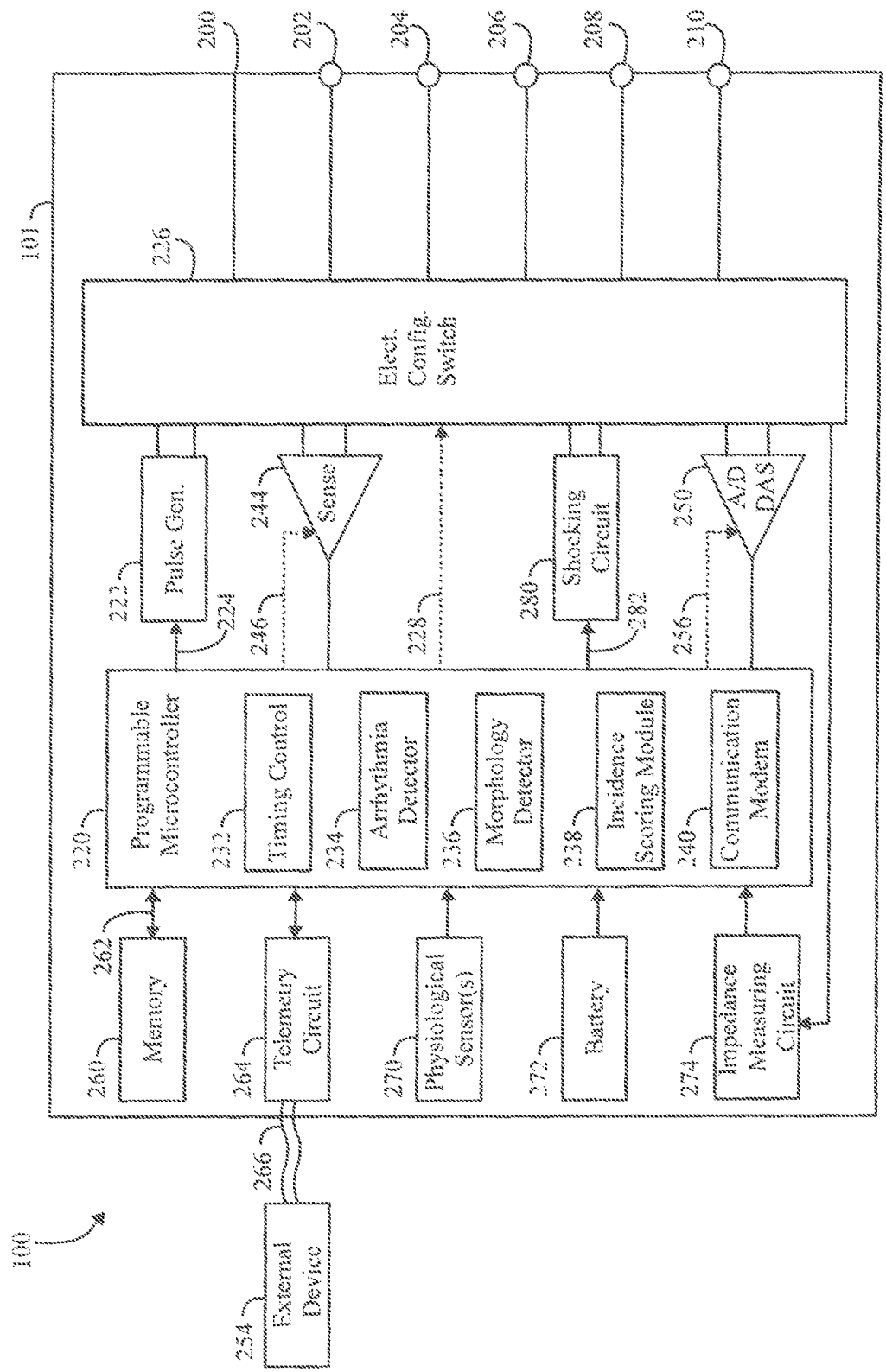
FIG. 2 shows an exemplary IMD that is configured to be implanted into the patient, in accordance with embodiments herein.

FIG. 2 shows a block diagram of an exemplary IMD 100 that is configured to be implanted into the patient. The IMD 100 may treat both fast and slow arrhythmias with stimulation therapy, including cardioversion, pacing stimulation, an implantable cardioverter defibrillator, suspend tachycardia detection, tachyarrhythmia therapy, and/or the like.

The IMD 100 has a housing 101 to hold the electronic/computing components. The housing 101 (which is often referred to as the "can," "case," "encasing," or "case electrode") may be programmably selected to act as the return electrode for certain stimulus modes. The housing 101 further includes a connector (not shown) with a plurality of terminals 200-210. The terminals may be connected to electrodes that are located in various locations within and about the heart. The type and location of each electrode may vary. For example, the electrodes may include various combinations of ring, tip, coil, shocking electrodes, and the like.

The IMD 100 includes a programmable microcontroller 220 that controls various operations of the IMD 100, including, cardiac monitoring and stimulation therapy. The microcontroller 220 includes a microprocessor (or equivalent control circuitry), one or more processors, RAM and/or ROM memory, logic and timing circuitry, state machine circuitry, and I/O circuitry. The IMD 100 further includes a ventricular pulse generator 222 that generates stimulation pulses for connecting the desired electrodes to the appropriate I/O circuits, thereby facilitating electrode programmability. The switch 226 is controlled by a control signal 228 from the microcontroller 220.

A pulse generator 222 is illustrated in FIG. 2. Optionally, the IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The IMD 100 includes sensing circuit 244 selectively coupled to one or more electrodes that perform sensing operations, through the switch 226 to detect the presence of cardiac activity in the chamber of the heart 111. The output of the sensing circuit 244 is connected to the microcontroller 220 which, in turn, triggers, or inhibits the pulse generator 222 in response to the absence or presence of cardiac activity. The sensing circuit 244 receives a control signal 246 from the microcontroller 220 for purposes of controlling the gain, threshold, polarization charge removal circuitry (not shown), and the timing of any blocking circuitry (not shown) coupled to the inputs of the sensing circuit 224.

In the example of FIG. 2, the sensing circuit 244 is illustrated. Optionally, the IMD 100 may include multiple sensing circuits 244, where each sensing circuit is coupled to one or more electrodes and controlled by the microcontroller 220 to sense electrical activity detected at the corresponding one or more electrodes. The sensing circuit 224 may operate in a unipolar sensing configuration or a bipolar sensing configuration.

The IMD 100 further includes an analog-to-digital (A/D) data acquisition system (DAS) 250 coupled to one or more electrodes via the switch 226 to sample cardiac signals across any pair of desired electrodes. The A/D converter 250 is configured to acquire intracardiac electrogram signals, convert the raw analog data into digital data and store the digital data for later processing and/or telemetric transmission to an external device 254 (e.g., a programmer, local transceiver, or a diagnostic system analyzer). The A/D converter 250 is controlled by a control signal 256 from the microcontroller 220.

The microcontroller 220 is operably coupled to a memory 260 by a suitable data/address bus 262. The programmable operating parameters used by the microcontroller 220 are stored in the memory 260 and used to customize the operation of the IMD 100 to suit the needs of a particular patient. The operating parameters of the IMD 100 may be non-invasively programmed into the memory 260 through a telemetry circuit 264 in telemetric communication via communication link 266 (e.g., MICS, Bluetooth low energy, and/or the like) with the external device 254.

The IMD 100 can further include one or more physiological sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the IMD 100, the physiological sensor(s) 270 may be external to the IMD 100, yet still, be implanted within or carried by the patient. Examples of physiological sensors might include sensors that, for example, sense respiration rate, pH of blood, ventricular gradient, activity, position/posture, minute ventilation (MV), and/or the like.

A battery 272 provides operating power to all of the components in the IMD 100. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the IMD 100 employs lithium/silver vanadium oxide batteries.

The IMD 100 further includes an impedance measuring circuit 274, which can be used for many things, including sensing respiration phase. The impedance measuring circuit 274 is coupled to the switch 226 so that any desired electrode and/or terminal may be used to measure impedance in connection with monitoring respiration phase. The IMD 100 is further equipped with a communication modem (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The microcontroller 220 further controls a shocking circuit 280 by way of a timing control 232. The shocking circuit 280 generates shocking pulses of low (e.g., up to 0.5 joules), moderate (e.g., 0.5-10 joules), or high energy (e.g., 11 to 40 joules), as controlled by the microcontroller 220. The shocking circuit 280 is optional and may be controlled by the microcontroller 220 by a control signal 282. Optionally, the shocking circuit 280 may not be implemented in the IMD 100.

Although not shown, the microcontroller 220 may further include other dedicated circuitry and/or firmware/software components that assist in monitoring various conditions of the patient's heart and managing pacing therapies. The microcontroller 220 further includes a timing control 232, an arrhythmia detector 234, a morphology detector 236 and an incidence scoring module 238. The timing control 232 is used to control various timing parameters, such as stimulation pulses (e.g., pacing rate), as well as to keep track of the timing of RR-intervals, refractory periods, blanking intervals, noise detection windows, evoked response windows, alert intervals, marker channel timing, and the like. The morphology detector 236 is configured to review and analyze one or more features of the morphology of CA signals. For example, in accordance with embodiments herein, the morphology detector 236 may analyze the morphology of detected R waves, where such morphology is then utilized to determine whether to include or exclude one or more beats from further analysis. For example, the morphology detector 236 may be utilized to identify non-conducted ventricular events, such as premature ventricular contractions, ventricular tachycardia and the like.

The arrhythmia detector 234 is configured to apply one or more arrhythmia detection algorithms for detecting arrhythmia conditions. By way of example, the arrhythmia detector 234 may apply various AF detection algorithms. For example, the arrhythmia detector 234 may apply the AF detection algorithm described in U.S. Pat. No. 8,121,675, entitled, "Device and method for detecting atrial fibrillation," the complete subject matter of which is incorporated herein by reference.

The incidence scoring module 238 is configured to track and score the occurrence of ventricular paced events, and based thereon derive one or more pacing incidents scores. The pacing incidents scores are then utilized by the microcontroller 220 to determine whether the arrhythmia detector 234 can reliably declare an AF episode or alternatively whether too many ventricular paced events have occurred within the CA signals. Additionally or alternatively, the incidence scoring module 238 may adjust one or more threshold parameters of the AF detection algorithm (e.g., RR interval variability thresholds) based on the pacing incidents scores.

Figure 3:
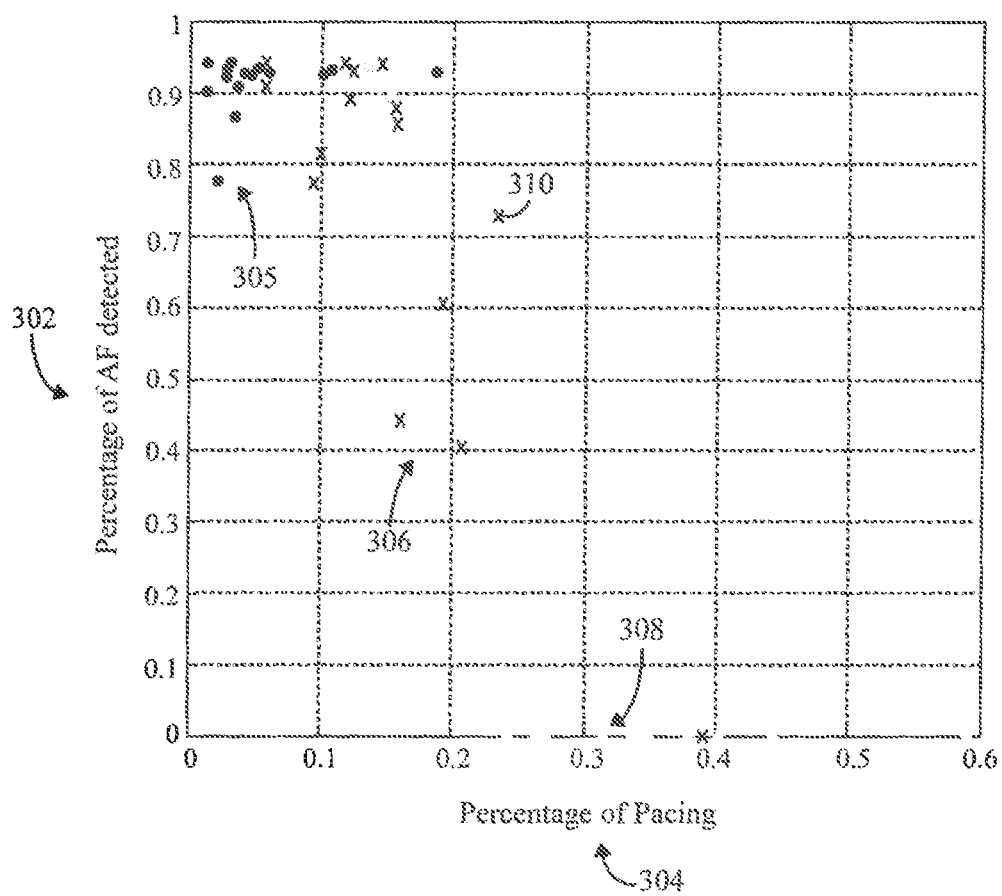
FIG. 3 illustrates a graphical example of AF detection accuracy affected by the percentage of pacing over an known AF detection method, in accordance with embodiments herein.
Figure 4:
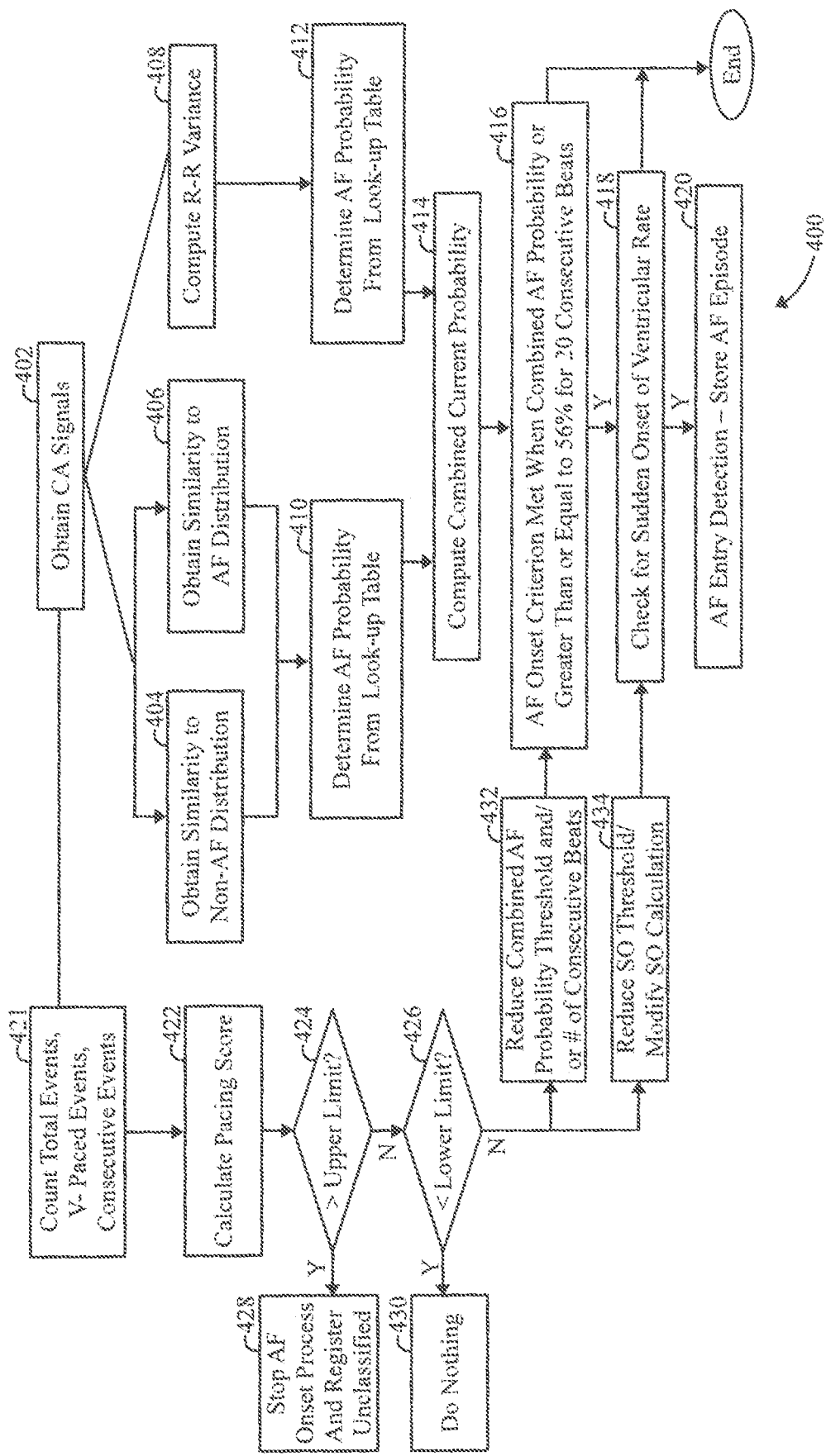
FIG. 4 illustrates a computer implemented process for adapting an AF onset detection algorithm in accordance with embodiments herein.

The arrhythmia detector 234, morphology detector 236 and incidence scoring module 238 operate in combination, as described herein (e.g., in connection with FIGS. 3 and 4). The microcontroller 220 collects CA signals for a collection window for a predetermined period of time or number of beats (e.g., one minute or 68 beats). The arrhythmia detector 234 detects R waves within the CA signals for the collection window. Optionally, the morphology detector 236 may analyze the morphology of the R waves in search of non-conducted ventricular events (PVCs or VTs). For example, the morphology detector 236 may compare a morphology of consecutive beats to one or more templates associated with normal/healthy R waves morphologies, PVC morphologies. VT morphologies, and the like. The morphology detector 236 may modify the CA signals by excluding beats that are declared to represent the non-conducted ventricular events (PVCs or VT) to to form nonconduction corrected CA signals to improve the specificity of the AF detection. Additionally or alternatively, the morphology detector 236 may determine to block or exclude the entire CA signal in the event that more than a predetermined number of the beats are declared as nonconductive ventricular events.

The incidence scoring module 238 tracks, within the original and/or non-conduction corrected CA signals, the incidence of ventricular paced events delivered by the IMD, and calculates a percentage of ventricular paced events within a certain amount of time or number of R waves. The incidence scoring module 238 also calculates a percentage of consecutive ventricular paced events (2 consecutive, 3 consecutive) within a certain amount of time or number of beats (e.g., 50-70 beats). Based on the foregoing calculations, the incidence scoring module 238 calculates a pacing incidences score.

The incidence scoring module 238 determines whether the AF detector can reliably detect/declare AF episodes from CA signals. In addition, the incidence scoring module 238 may determine, based on the pacing incidents score, an amount to which to adjust one or more parameters of the AF detection algorithm in order to better account for a presence of paced events within the CA signals being analyzed. For example, the incidence scoring module 238 compares the pacing incidence score with one or more thresholds. Responsive to a score exceeding a limit of 30%, the incidence scoring module 238 blocks or directs the AF detector from declaring CA signals to exhibit AF. Additionally or alternatively, the incidence scoring module 238 may mark the CA signals as "unclassified," as the score indicates that a heavy burden of ventricular paced events may prevent reliable AF detection. Responsive to a score below 10%, the incidence scoring module 238 instructs (or permits) the arrhythmia detector 234 to continue the AF detection process as the score indicates that an extent/degree of ventricular paced events is negligible. Responsive to a score between 10-30%, the incidence scoring module 238 may adjust threshold values, utilized by the AF detection algorithm, for R-R interval variability.

FIG. 3 illustrates a graphical example of AF detection accuracy affected by the percentage of pacing over an known AF detection method, in accordance with embodiments herein. As illustrated in connection with FIG. 3, as the percentage of ventricular paced events increases, the accuracy of AF episode detection and AF burden/duration detection decreases. Therefore, when AF duration is not properly detected, AF burden is under-estimated. The chart plots a series of data points in connection with different programmed ventricular pacing rates. EGM strips tested in the simulation were obtained for fifteen 5-minute long AF episodes. The EGM strips for each AF episode included a series of beats. The timing of beats in the fifteen episodes were modified, through modeling, to replicate ventricular paced events utilizing three different base ventricular pacing rates, namely 60 bpm, 70 bpm and 80 bpm. The modified EGM strips were again analyzed by the AF detection algorithm for AF episodes. For example, the fifteen EGM strips, modified for pacing at 60 bpm, were analyzed to see how many of the fifteen strips were again declared to exhibit AF, and the results are denoted in FIG. 3 with dark circular dots. The fifteen EGM strips, modified for pacing at 70 bpm, were analyzed to see how many of the 15 strips were again declared to exhibit AF and the results are denoted in FIG. 3 with "X" dots. The fifteen EGM strips, modified for pacing at 80 bpm, were analyzed to see how many of the 15 strips were again declared to exhibit AF and the results are denoted in FIG. 3 with light circular dots.

The horizontal axis 304 representing a percentage of a total number of cardiac events/beats, during which ventricular pacing was delivered. The vertical axis 302 represents a percentage of duration during which AF was correctly declared by the AF detection algorithm. For example, the data point 305 along the vertical axis 302 indicates that 78% of the entire EGM strip was detected as AF by the algorithm. As a further example, data point 310 indicates that, for the corresponding number of beats from the EGM strips, approximately 24% of the beats received ventricular pacing (based on a programmed ventricular pacing rate of 70 bpm), while the AF detection algorithm accurately declared 73% of the AF duration. From the data points in FIG. 3, it is shown that when relatively few beats receive ventricular pacing (e.g., <10%), all of the AF episodes are detected and the detected AF durations are greater than 75% of the true AF duration. Alternatively, when a larger number of the beats receive ventricular pacing (e.g., >30%), none of the AF episodes are detected. When the percentage of beats that are paced is moderate (e.g., 10-30%), some of the AF episodes are properly detected, while some of the AF episodes are not properly detected or are detected but with a much shorter duration.

In general, the data points show a high degree of accuracy in AF detection when a relatively small percentage of the beats receive ventricular pacing. As the percentage of beats that are paced increases (e.g. in the collection 306), the AF detection accuracy drops to between 40% and 80%. When the percentage of beats that are paced increases above 30% (e.g. the collection at 308), the AF detection accuracy substantially drops to less than 10%. The data from FIG. 3 illustrates that, by utilizing the metrics described herein for tracking of ventricular paced events, embodiments herein avoid attempting to apply in AF detection algorithm in a situation in which the AF detection algorithm will not provide accurate results. Accordingly, embodiments herein avoid a determination of AF durations that are lower than the true AF duration, which is not preferred for tracking AF burden. As one example, when less than 10% of the beats receive ventricular pacing, and AF detection algorithm may be allowed to analyze the CA signals without modifying the parameters thereof. Otherwise, when more than 10% of the beats receive ventricular pacing, parameters of the AF detection algorithm may be modified, such as by adjusting thresholds for RR intervals in order to maintain more accurate detection of the AF episodes and the AF duration.

FIG. 4 illustrates a computer implemented process and/or method 400 for adapting an AF onset detection algorithm in accordance with embodiments herein. The operations of FIG. 4 may be repeated periodically or in response to detection of particular criteria, such as detection of potential atrial fibrillation episodes or otherwise. The operations of FIG. 4 increase AF detection specificity.

At 402, the one or more processors obtain CA signals (e.g., an EGM strip) for multiple beats over a predetermined period of time. As one example, the CA signals may be collected for a one-minute interval, during which multiple successive cardiac beats occur. Flow branches from 402 along two parallel processing paths, namely along an AF onset detection path corresponding to 404-420 and an adaptation path corresponding to 422-434. The operations at 404-420 generally represent an AF onset detection algorithm that may be implemented based on RR interval distribution and instability. For example, the operations at 404-420 may implement the AF onset detection algorithm described in U.S. Pat. No. 8,121,675. The operations at 422-434 describe a process for tracking ventricular paced events and based thereon adapting the AF onset detection algorithm. Among other things, the operations at 422-434 determine whether a number of ventricular paced events within a series of beats may unduly interfere with a determination of AF duration as calculated by AF onset detection algorithm.

At 404, the one or more processors detect the R waves within the CA signals and analyze a distribution thereof to obtain similarities to a non-AF distribution. At 406, the one or more processors analyze a distribution of the CA signals and obtain similarities to an AF distribution. The processors perform the operations at 404, 406 for each beat, by looking at an RR interval of a current beat and the RR intervals of a previous series of beats (e.g., 64 beats) to obtain the similarities to an AF distribution and/or a non-AF distribution. At 410, the one or more processors determine a first AF probability based on the similarities to the AF distribution and non-AF distribution. For example, the AF probability may be obtained from a lookup table stored in the memory 220. By way of example, at 404, 406, 410, the processors may use a Markov Chain model to compare similarity of RR interval transitions in the current beat and previous series of beats to both AF and non-AF templates.

In parallel with the operations at 404, 406 and 410, the one or more processors also perform the operations at 408, 412. At 408, the one or more processors compute an R-R variance across the beats within the CA signals (e.g., 50-60 beats and/or 1-2 minutes). At 412, the one or more processors determine a second AF probability, based on the RR variance, from a lookup table to obtain a second probability based on the computed R-R interval variance. For example, the second AF probability may be based on the computed RR interval variance (at 408) to differentiate between random and patterned changes in the RR interval, such as in connection with bigeminy.

Next, the operations at 414-420 determine whether AF onset for an AF episode has begun. At 414, the one or more processors combine the first and second probabilities. For example, the first and second probabilities may be combined through averaging or another mathematical operation to form a combined AF probability. At 416, the one or more processors determine whether the combined AF probability satisfied one or more AF onset criteria. For example, the AF onset criteria may be met when the combined AF probability satisfied a threshold, such as when the combined AF probability is greater than or equal to a threshold (e.g., 50-60%) for a predetermined number of consecutive beats (e.g., 20 consecutive beats). If so, AF onset is declared and flow continues to 418. If not, AF onset is not declared and the process ends. For example, AF onset may not be declared when the combined AF probability is below the probability threshold or above the probability threshold but for too few consecutive beats.

At 418, the one or more processors determine whether sudden onset (SO) of an accelerated ventricular rate has occurred. For example, the processors may calculate an instantaneous RR interval for a current beat and an average RR interval for a moving average for a predetermined number of prior beats (e.g., 4-6 prior beats). The processors then analyze a relation between the instantaneous and average RR intervals. When the relation between the instantaneous and average RR intervals exceeds an SO cut off threshold, the processors determined that the present beat is indicative of a sudden onset of an accelerated ventricular rate. Optionally, the processors may search for an indication of sudden onset for a predetermined number of beats out of the total beats (e.g., 16 out of 64). When the relation between the instantaneous and average RR intervals exceeds the SO cut off threshold for the predetermined number of beats (e.g., 16 out of 64), sudden onset is declared, and flow continues to 420. Alternatively, when the relation between the instantaneous and average RR intervals falls below the SO cut off threshold, the processors determined that the present beat is not indicative of sudden onset and the process of FIG. 4 ends.

At 420, the one or more processors declare entry of an AF episode and/or stores a beginning time for the AF episode in the memory 160.

Figure 5:
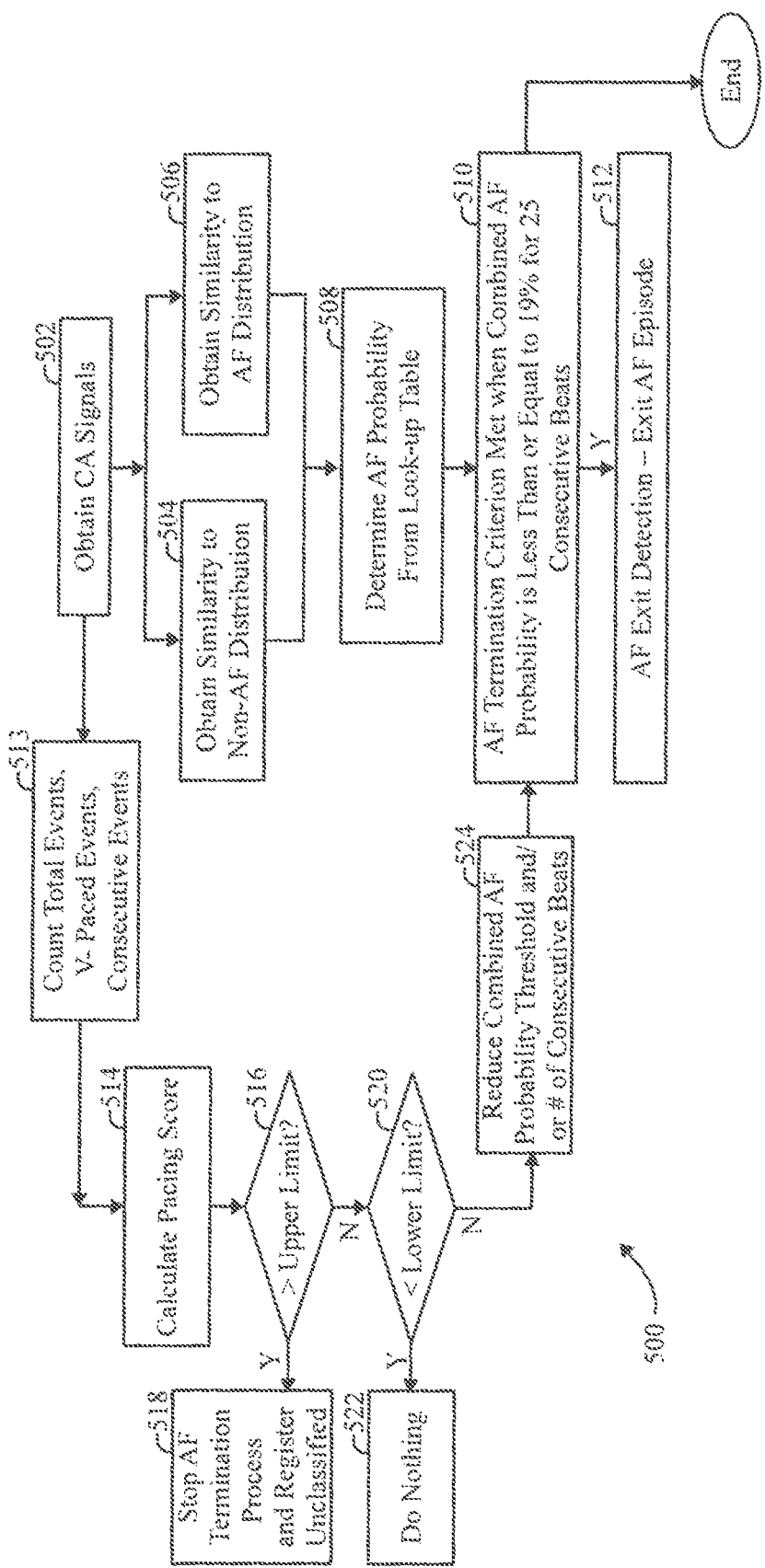
FIG. 5 illustrates a computer implemented process for adapting an AF exit/termination detection algorithm in accordance with embodiments herein.

While the operations of FIG. 4 end at 420, it is understood that the AF detection algorithm continues to monitor subsequent CA signals to track a duration of the AF episode until identifying an end/termination of the AF episode as explained hereafter in connection with FIG. 5. When the AF exit criteria are satisfied, the processors may record information concerning the end of an AF episode. When the AF episode terminates, the one or more processors record the ending time for the AF episode and/or the number of beats during the AF episode that exhibited AF, thereby defining the overall AF burden. The AF burden is defined as the amount of time in which a patient experiences AF over the monitoring period.

The IMD may be configured to deliver a therapy to terminate the AF episode and/or simply record the occurrence of the AF episode. The foregoing process at 404-420 iteratively repeat to declare onset of an AF episode and termination of an AF episode.

Next the operations at 422-434 are described to adapt the AF onset detection process, such as to avoid a false determination of AF entry and/or no AF entry by the operations at 404-420.

At 421, the one or more processors analyzes the CA signals to count various types of events therein. For example, the processors count a total number of events in the CA signals, count a number of V-paced events in the CA signals, and count a number of consecutive V-paced events in the CA signals. For example, a one minute EGM strip of CA signals may include 70-100 events, from which trend events may represent the paced events. The V-paced events may occur as "singles" preceded and succeeded by non-paced events. Optionally, one or more of the paced events may be preceded or succeeded by one or more of the paced events. The processors count the number of consecutive V-paced events as a separate count within the CA signals. Additionally or alternatively, the processors may separately bin/count different combinations of consecutive V-paced events, such as to count a number of times that 2 consecutive V-paced events occurred, count a number of times that 3 consecutive V-paced events occurred, and the like.

Optionally, at 421, the one or more processors may adjust the count of the total number of beats based on a morphology discrimination. For example, the processors may utilize morphology discrimination to exclude beats from the counts used to calculate the pacing incidence scores. For example, the processors may compare each non-paced event to a PVC morphology template and/or a VT morphology template. When the non-paced event matches the PVC or VT morphology template, the processors may blank or remove the beat from the count of the total number of events. The foregoing process allows the one or more processors to identify a PVC or VT in the CA signals, declare the beat to represent a non-conducted event and remove the non-conducted event from the counts used for the various pacing incidence scores. The one or more processors adjust (reduce) the total number of beats for calculating the pacing incidence score based on the non-conducted paced events.

At 422, the one or more processors calculate one or more pacing incidence scores based on the various counts of the events. For example, the incidence scoring module 238 calculates a total pacing incidence score as a percent of V-paced events (ventricular pacing) out of a total number of beats. Additionally or alternatively, the incidence scoring module 238 may calculate a consecutive pacing incidence score as a percent of consecutive V-paced events out of the total number of beats. The total pacing incidence score and the consecutive pacing incidence score may be combined to form an overall pacing incidence score, such as through averaging or other mathematical combinations.

Additionally or alternatively, when calculating the overall pacing incidence score, the one or more processors may apply different weights to the total pacing incidence score (PIS) and consecutive pacing incidence score (e.g., $PIS_{overall}=40\% \times PIS_{total}+60\% \times PIS_{consec}$). Additionally or alternatively, the one or more processors may apply different weights to different numbers of consecutive pacing incidence scores, such as a first weight for two consecutive PIS, and the like.

At 424, the one or more processors determine whether the overall pacing incidence score is above an upper limit. For example, the upper limit may be set at 30%. When the overall pacing incidence score exceeds the upper limit, flow moves to 428. At 428, the one or more processors terminate or halt the AF onset determination process at 404-420 and register the CA signals as "unclassified". By registering the CA signals is unclassified, the processors indicate that the CA signals include an amount of pacing events to extensive to accurately analyze the CA signals for AF onset. Additionally, the duration of "unclassified" periods may be reflected in AF burden calculation. When an "unclassified" condition does not exist, AF burden is calculated by the duration in AF over the monitoring period. When the "unclassified" condition does exist, the duration in AF, not AF, and in the "unclassified" condition are calculated. Two AF burden numbers can be calculated, one with AF duration over total monitoring duration, the other with AF duration over the eligible monitoring duration calculated by the total monitoring duration minus "unclassified" period.

Returning to 424, when the overall pacing incidence score does not exceed the upper limit, flow continues to 426. At 426, the one or more processors determine whether the overall pacing incidence score is below a lower limit. For example, the lower limit may be at 10% of the overall pacing incidence score. When the overall pacing incidence score is below the lower limit, flow moves to 430. At 430, the one or more processors permit the AF onset detection process at 404-422 to continue without adjusting detection parameters as the processors have determined that an amount of pacing events is relatively low and should have little to no impact on accuracy of the AF onset detection process.

Returning to 426, when the overall pacing incidence score is above the lower limit, flow continues to 432, 434. The operations at 432, 434 adjust one or more parameters of the AF onset detection process.

At 432, the one or more processors reduce one or more of the AF onset criteria, such as reducing the combined AF probability threshold and/or the number of consecutive beats to satisfy the threshold. By way of example, the probability threshold and/or number of consecutive beats may be reduced by predetermined amounts. For example, the one or more processors may reduce the AF probability threshold to below 50% (e.g., 15%, 20%, 40%) and/or reduce a number of consecutive beats to below 20 (e.g., 10, 15). Additionally or alternatively, the probability threshold and/or number of consecutive beats may be reduced by an adjustable amount depending upon a relation of the overall pacing incidence score to the upper or lower limits. For example, when the upper limit is 30% and the overall pacing incidence score is 28%, the probability threshold and number of consecutive beats may be adjusted by relatively larger amounts. Alternatively, when the upper limit is 30% and the overall pacing incidence score is 12%, the probability threshold and number of consecutive beats may be reduced by relatively smaller amounts.

At 432, one or more of the overall, total and consecutive pacing incidence scores may be utilized. For example, the total pacing incidence score of the V-paced events may be used to modulate the probability threshold, while the consecutive pacing incidence score of the consecutive V-paced events is used to modulate a number of consecutive beats. Additionally or alternatively, when the one or more processors detects a predetermined number (e.g., three or more) consecutive V-paced events beats, the processors may exclude the corresponding V-paced events from the Markov Chain model utilized to calculate AF probability.

At 434, the one or more processors modify the SO cut off threshold. For example, the processors may reduce the SO off threshold by a predetermined amount and/or percentage, or based on other criteria. For example, the one or more processors may adjust the sudden onset cut off threshold relative to below 100 ms of the R-R interval (e.g., 90 ms, 80 ms, 70 ms) and/or V-paced events. Optionally, the processors may adjust the number of beats out of the total beats that satisfy the SO cut off threshold before declaring sudden onset. For example, when the initial number is set to 16, at 434, the number may be reduced to 12 or fewer for the number of beats to satisfy the SO cut off threshold before declaring sudden onset.

Additionally or alternatively, at 434, the processors may determine to modify the SO calculation operation (at 418) utilized to declare sudden onset. By way of example, the processors may review all or a portion of the beats in the CA signals (e.g., 60 successive beats) and calculate a number of the beats that exhibited a sudden onset value that exceeds a predetermined SO limit (e.g., greater than 100 ms). The processors counts the number of beats that exhibited sudden onset that exceeded the SO limit and, when the count exceeds an SO count limit, then the processors declare sudden onset to be present. Accordingly, the operation at 434 may change the SO calculation, as compared to the operation at 418, in that the operation at 434 no longer compares a relation between instantaneous and average RR intervals to an SO cut off threshold.

Optionally, the sudden onset criteria may be modified to ignore any paced events that immediately precede a trigger.

FIG. 5 illustrates a computer implemented process and/or method 500 for adapting an AF exit/termination detection algorithm in accordance with embodiments herein. The operations of FIG. 5 may be repeated periodically or in response to detection of particular criteria, such as detection of potential atrial fibrillation episodes or otherwise.

At 502, the one or more processors obtain CA signals (e.g., an EGM strip) for multiple beats over a predetermined period of time. As one example, the CA signals may be collected for a one-minute interval, during which multiple successive cardiac beats occur. Flow branches from 502 along two parallel processing paths, namely along the AF exit detection path corresponding to 504-512 and the adaptation path corresponding to 513-524. The operations at 504-512 generally represent an AF exit detection algorithm that may be implemented based on RR interval distribution and instability. For example, the operations at 504-514 may implement the AF exit detection algorithm described in U.S. Pat. No. 8,121,675. The operations at 513-524 describe a process for tracking ventricular paced events and based thereon adapting the AF exit detection algorithm. Among other things, the operations at 514-524 determine whether a number of ventricular paced events within a series of beats may unduly interfere with a determination of AF duration as calculated by AF exit detection algorithm.

At 504, the one or more processors detect the R waves within the CA signals and analyze a distribution thereof to obtain similarities to a non-AF distribution. At 506, the one or more processors analyze a distribution of the CA signals and obtain similarities to an AF distribution. The processors perform the operations at 504, 506 for each beat, by looking at an RR interval of a current beat and the RR intervals of a previous series of beats (e.g., 64 beats) to obtain the similarities to an AF distribution and/or a non-AF distribution. At 508, the one or more processors determine an AF probability based on the similarities to the AF distribution and non-AF distribution. For example, the AF probability may be obtained from a lookup table stored in the memory 160. By way of example, at 504, 506, 508, the processors may use a Markov Chain model to compare similarity of RR interval transitions in the current beat and previous series of beats to both AF and non-AF templates.

At 510, the one or more processors determine whether AF exit for an AF episode has occurred. For example, the processors may determine whether an AF exit criteria has been met by the AF probability. For example, the AF exit criteria may indicate that, when the AF probability is less than 19% for 25 consecutive beats, and AF episode may be declared to have terminated. When the AF exit criteria are not met, the process of FIG. 5 ends without declaring termination of a current AF episode and the AF detection process continues to monitor a current AF episode. When the AF exit criteria are met, flow continues to 512.

At 512, the one or more processors declare AF exit/termination to occur for the current AF episode. The processors record information related to termination of the present AF episode, such as the point in time at which termination occurred.

Next the operations at 513-524 are described to adapt the AF exit detection process, such as to avoid a false determination of AF exit and/or no AF exit by the operations at 504-512.

At 513, the one or more processors analyzes the CA signals to count various types of events therein. For example, the processors count a total number of events in the CA signals, count a number of V-paced events in the CA signals, and count a number of consecutive V-paced events in the CA signals. For example, a one minute EGM strip of CA signals may include 70-100 events, from which trend events may represent the paced events. The V-paced events may occur as "singles" preceded and succeeded by non-paced events. Optionally, one or more of the paced events may be preceded or succeeded by one or more of the paced events. The processors count the number of consecutive V-paced events as a separate count within the CA signals. Additionally or alternatively, the processors may separately bin/count different combinations of consecutive V-paced events, such as to count a number of times that 2 consecutive V-paced events occurred, count a number of times that 3 consecutive V-paced events occurred, and the like.

Optionally, at 513, the one or more processors may adjust the count of the total number of beats based on a morphology discrimination as described above in connection with the operation at 421 in FIG. 4.

At 514, the one or more processors calculate one or more pacing incidence scores based on the various counts of the events. For example, the incidence scoring module 238 calculates a total pacing incidence score as a percent of V-paced events (ventricular pacing) out of a total number of beats. Additionally or alternatively, the incidence scoring module 238 may calculate a consecutive pacing incidence score as a percent of consecutive V-paced events out of the total number of beats. The total pacing incidence score and the consecutive pacing incidence score may be combined to form an overall pacing incidence score, such as through averaging or other mathematical combinations.

At 516, the one or more processors determine whether the overall pacing incidence score is above an upper limit. For example, the upper limit may be set at 30%. When the overall pacing incidence score exceeds the upper limit, flow moves to 518. At 518, the one or more processors terminate or halt the AF exit determination process at 504-512 and register the CA signals as "unclassified". By registering the CA signals as unclassified, the processors indicate that the CA signals include an amount of pacing events to extensive to accurately analyze the CA signals for AF exit.

Returning to 516, when the overall pacing incidence score does not exceed the upper limit, flow continues to 520. At 520, the one or more processors determine whether the overall pacing incidence score is below a lower limit. For example, the lower limit may be at 10% of the overall pacing incidence score. When the overall pacing incidence score is below the lower limit, flow moves to 522. At 522, the one or more processors permit the AF exit detection process at 504-512 to continue without adjusting detection parameters as the processors have determined that an amount of pacing events is relatively low and should have little to no impact on accuracy of the AF exit detection process.

Returning to 520, when the overall pacing incidence score is above the lower limit, flow continues to 524. The operations at 524 adjust one or more parameters of the AF exit detection process. At 524, the one or more processors adaptively adjust the AF probability threshold, and/or the number of consecutive beats to satisfy the AF probability threshold. For example, the one or more processors may reduce the AF probability threshold from 19% to 15%, 10% and the like. Additionally or alternatively, the one or more processors may reduce the number of consecutive beats to satisfy the AF probability threshold from 25 consecutive beats to 20 consecutive beats, 15 consecutive beats and the like. Optionally, the one or more processors may increase the AF probability threshold and/or increase the number of consecutive beats (e.g., 30 consecutive beats, 40 consecutive beats). The operations at 524 adjust the AF exit probability threshold of the AF exit detection process to be rendered the process more critical before declaring AF exit (e.g., make it harder to determine AF exit).

It is recognized that the foregoing numeric values are merely examples and that alternative values may be utilized.

Additionally or alternatively, the total pacing incidence score and the consecutive pacing incidence score may be applied differently in connection with adjusting AF onset criteria and/or adjusting AF exit criteria. For example, the total pacing incidence score may be utilized in connection with modulating the AF onset probability threshold and/or the AF exit probability threshold. The consecutive pacing incidence score may be utilized to modulate a number of consecutive beats to satisfy the corresponding AF onset or AF exit probability threshold.

Optionally, when runs of three or more consecutive paced beats are identified, the corresponding RR intervals may be excluded from any AF probability calculations based on Markov Chain models. When RR intervals for three or more consecutive paced beats are excluded, alternative earlier beats may be retained and utilized in the calculation, effectively suspending AF entry or AF exit instead of adjusting a threshold.

Closing

The various methods as illustrated in the Figures and described herein represent exemplary embodiments of methods. The methods may be implemented in software, hardware, or a combination thereof. In various methods, the order of the steps may be changed, and various elements may be added, reordered, combined, omitted, modified, etc. Various steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the internet, an intranet, an extranet, a public switched telephone network, an infrared network, a wireless network, a satellite network, and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers. Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A computer implemented method for detecting arrhythmias in cardiac activity, comprising:
    under control of one or more processors configured with specific executable instructions,
    obtaining cardiac activity (CA) signals that includes a series of beats, the CA signals including paced events;
    identifying the paced events in the CA signals;
    determining a score based on an amount of paced events; and
    adjusting at least one parameter of an atrial fibrillation (AF) detection process based on the score.

2. The method of claim 1, further comprising analyzing the CA signals to identify a i) first count of a total number of events in the CA signals, ii) second count of a number of V-paced events in the CA signals and iii) third count of a number of consecutive V-paced events in the CA signals, the score based on at least one of the first, second and third counts.

3. The method of claim 2, further comprising determining an overall pacing incidence score based on a weighted combination of a total pacing incidence score and a consecutive pacing incidence score, the total pacing incidence score based on a relation between the number of the paced events and the total number of events, the consecutive pacing incidence score based on the number of consecutive V-paced events and the total number of events.

4. The method of claim 1, further comprising comparing the score to an upper limit and based on the comparing, stopping an AF onset process and registering the CA signals as unclassified.

5. The method of claim 1, wherein the adjusting further comprises at least one of i) adjusting an AF onset criteria, ii) adjusting an AF exit criteria, iii) adjusting a sudden onset (SO) criteria or iv) modify an SO calculation.

6. The method of claim 5, further comprising, when the score is between the upper and lower limits, performing at least one of the adjusting operations.

7. The method of claim 5, wherein the adjusting further comprises adjusting an AF onset criteria by reducing at least one of an AF probability threshold or a number of consecutive beats to satisfy the AF probability threshold.

8. The method of claim 5, wherein the adjusting further comprises adjusting an AF exit criteria by reducing at least one of an AF probability threshold or a number of consecutive beats to satisfy the AF probability threshold.

9. The method of claim 5, wherein the adjusting further comprises modifying the SO calculation by calculating a number of beats in the CA signals that exhibit a sudden onset value that exceeds a predetermined SO limit, and, when the number of beats exceeds an SO count limit, declaring sudden onset to be present in the CA signals.

10. The method of claim 1, wherein the determining operation further comprises identifying non-conducted ventricular events in the CA signals, counting a total number of events in the CA signals, adjusting the counter by removing the non-conducted ventricular events from the count and determining the score based on the paced events and the count of the total number of events in the CA signals adjusted for the non-conducted ventricular events.

11. The method of claim 1, further comprising delivering stimulation pulses at one or more electrodes in connection with the paced events.

12. A system for discriminating rhythm patterns in cardiac activity, the system comprising:
   at least one processor; and
   a memory coupled to the at least one processor, wherein the memory stores program instructions, wherein the program instructions are executable by the at least one processor to:
   obtain cardiac activity (CA) signal that includes far field CA signals for a series of beats, the CA signals including paced events;
   identify the paced events in the CA signals;
   determine a score based on the paced events; and
   adjust at least one parameter of an atrial fibrillation (AF) detection process based on the score.

13. The system of claim 12, wherein the processor is further configured to analyze the CA signals to identify a i) first count of a total number of events in the CA signals, ii) second count of a number of V-paced events in the CA signals and iii) third count of a number of consecutive V-paced events in the CA signals, the score based on at least one of the first, second and third counts.

14. The system of claim 12, wherein the processor is further configured to determine an overall pacing incidence score based on a weighted combination of a total pacing incidence score and a consecutive pacing incidence score, the total pacing incidence score based on a relation between the number of the paced events and the total number of events, the consecutive pacing incidence score based on the number of consecutive V-paced events and the total number of events.

15. The system of claim 12, wherein the processor is further configured to compare the score to an upper limit and based on the comparison, stop an AF onset process and registering the CA signals as unclassified.

16. The system of claim 12, wherein the processor is further configured to at least one of i) adjust an AF onset criteria, ii) adjust an AF exit criteria, iii) adjust a sudden onset (SO) criteria or iv) modify an SO calculation.

17. The system of claim 16, wherein the processor is further configured to, when the score is between the upper and lower limits, perform at least one of the adjusting operations.

18. The system of claim 16, wherein the processor is further configured to adjust an AF onset criteria by reducing at least one of an AF probability threshold or a number of consecutive beats to satisfy the AF probability threshold.

19. The system of claim 16, wherein the processor is further configured to adjust an AF exit criteria by reducing at least one of an AF probability threshold or a number of consecutive beats to satisfy the AF probability threshold.

20. The system of claim 16, wherein the processor is further configured to modify the SO calculation by calculating a number of beats in the CA signals that exhibit a sudden onset value that exceeds a predetermined SO limit, and, when the number of beats exceeds an SO count limit, declare sudden onset to be present in the CA signals.

21. The system of claim 12, wherein the processor is further configured to identify non-conducted ventricular events in the CA signals, counting a total number of events in the CA signals, adjust the counter by removing the non-conducted ventricular events from the count and determine the score based on the paced events and the count of the total number of events in the CA signals adjusted for the non-conducted ventricular events.

22. The system of claim 12, further comprising one or more electrodes configured to deliver stimulation pulses in connection with the paced events.

* * * * *